United States Patent [19]

Burdick et al.

[11] Patent Number: 5,102,446
[45] Date of Patent: Apr. 7, 1992

[54] NO-TILL LIQUID HERBICIDE AND FERTILIZER SUSPENSION

[75] Inventors: Charles L. Burdick, Landenberg, Pa.; Jashawant J. Modi, Hockessin, Del.

[73] Assignee: Aqualon Company, Wilmington, Del.

[21] Appl. No.: 579,715

[22] Filed: Sep. 10, 1990

Related U.S. Application Data

[63] Continuation-in-part of Ser. No. 473,410, Feb. 1, 1990.

[51] Int. Cl.$^5$ .................. A01N 43/40; A01N 59/26; C05B 7/00
[52] U.S. Cl. .......................... 71/94; 71/34; 71/82; 71/36; 71/65
[58] Field of Search .................. 71/94, 34, 80, 82

[56] References Cited

U.S. PATENT DOCUMENTS

| | | | |
|---|---|---|---|
| 2,972,528 | 2/1961 | Brian et al. | 71/94 |
| 3,526,495 | 9/1970 | Philen, Jr. et al. | 71/34 |
| 3,679,390 | 7/1972 | Young | 71/29 |
| 4,056,381 | 11/1977 | Kenton | 71/36 |
| 4,325,763 | 2/1982 | Stoller et al. | 71/29 |
| 4,336,053 | 6/1982 | Kenton | 71/40 |
| 4,859,208 | 8/1989 | Clare | 8/557 |
| 4,874,854 | 10/1989 | Colegrove et al. | 536/114 |

OTHER PUBLICATIONS

Parochetti, J. V., "Effect on no-tillage cover crops by pariquat . . . " etc. Proc. Northeast Weed Sci. Soc., 1978, 32, 36–43, CA88:184497.

*Primary Examiner*—Glennon H. Hollrah
*Assistant Examiner*—B. Bembenick
*Attorney, Agent, or Firm*—James K. Luchs

[57] ABSTRACT

A liquid fertilizer composition suitable for no-till farming contains a stabilizing amount of an admixture of calcium chloride and ammonium polyphosphate or similar nitrogen/phosphorous source in addition to a herbicide. As an improvement over clay suspensions, this liquid fertilizer can be used for one pass planting and herbicide application. Higher amounts of potash can be incorporated in the liquid fertilizer along with sulphur and nitrogen nutrients.

12 Claims, No Drawings

NO-TILL LIQUID HERBICIDE AND FERTILIZER SUSPENSION

This is a continuation-in-part of application Ser. No. 07/473410, filed Feb. 1, 1990.

FIELD OF THE INVENTION

This invention relates to liquid applications of fertilizer and herbicides for agriculture. In particular, the invention relates to the use of calcium chloride as a liquid suspension agent.

BACKGROUND OF THE INVENTION

The high levels of productivity achieved in modern agriculture have been largely the result of quite recent knowledge gained on effective means of applying sprays of fertilizers and herbicides. No-till farming is a new area in which soil is preserved and fertilizer requirements lowered by killing residual plants with a topical herbicide and using a seed drill to insert seed and spray nozzles to apply liquid fertilizer. But even this method of farming is limited by the requirement for separate applications of herbicide and fertilizer due to the incompatibility of the herbicide with the fertilizer suspending agent. As a result, two passes are required over the field instead of one which would be possible if a new suspending agent were available, which was not incompatible with the herbicide. U.S. Pat. No. 4,874,854 discloses comparative examples of polymers which are incompatible with the herbicide Paraquat ®.

U.S. Pat. Nos. 3,526,495, 3,679,390 and 4,315,763 teach that a wide variety of calcium salts cause gelling and thickening of fertilizers, similar to iron salts as described in U.S. Pat. Nos. 4,056,381 and 4,336,053. The first three references teach the equivalency of calcium chloride with other calcium salts, while a combination of all five references would suggest to a person of ordinary skill in the art that both calcium and iron salts can perform the same functions as fertilizer suspending agents. U.S. Pat. No. 4,118,218 discloses a process for preparing granular herbicidal compositions using an inert sodium or calcium chloride carrier.

U.S. Pat. No. 3,526,495 and U.S. Pat. No. 3,679,390 further illustrate that the present invention represents a long sought after result on which considerable time and effort has been expended. Whereas all prior art practitioners had the same goals and all materials were readily available, their disclosures all teach away from the discovery contained herein.

When clay is used as a suspending agent for fertilizer, the suspension produced has limited stability and tends to settle in about 24 hours. Thus, when trucks are not able to go into fields to spray the liquid fertilizer because of rain, it is necessary to unload the trucks and remix the liquid fertilizer. Therefore, it would be an advance in the state-of-the-art to have a liquid fertilizer composition which would not settle even if weather or mechanical delays put off field application.

A separate problem with clay suspensions is that they are difficult to prepare. While clay is a readily available and low cost material, preparation of the clay suspension is both time consuming and labor intensive. Thus it would be a further advance to be able to use a low cost and readily available suspension agent which could avoid the shortcomings of clay.

Clay is known to be a useful absorbent. However, this property would be detrimental if clay removed effective amounts of herbicide from a suspension. Thus a new type of suspension in which both fertilizer and herbicide could be applied from one composition would be a monumental advance for agriculture.

A further disadvantage of prior art clay suspensions of liquid fertilizers is the inability to incorporate desirable quantities of potash (potassium chloride) without encountering precipitation problems. As a practical limit it is difficult to prepare a clay suspension containing more than 10% by weight potash. Thus, the availability of a suspending agent which would allow incorporation of more than 10% by weight potash in the liquid fertilizer would be a significant advance. It would not have been apparent to employ calcium chloride for such a purpose in view of literature reports that precipitation rather than suspension would occur.

It is known that individual calcium salts are capable of performing unique functions; wherein other calcium salts are ineffective. U.S. Pat. No. 4,859,208 discloses and claims calcium citrate in a print paste composition.

SUMMARY OF THE INVENTION

The invention provides a liquid fertilizer composition which can additionally contain a herbicide in which a suspending agent is produced by mixing ammonium polyphosphate or a nitrogen and phosphate containing composition with calcium chloride prior to the addition of potash.

The process of the invention involves the steps:

(1) mixing calcium chloride with ammonium polyphosphate or a similar nitrogen and phosphorus composition for a time sufficient to prepare a solution; and (2) adding potash (potassium chloride) to the solution to prepare a storage stable liquid fertilizer suspension; and (3) adding an effective amount of a herbicide such as Paraquat ® or Gramoxone ® topical herbicide or equivalent.

Water may be added as a separate addition in step (2) and the process may be performed at ambient temperature.

The composition and process of the invention have further utility when additions of other nitrogen and sulphur sources and/or herbicide are incorporated in a storage stable liquid which can be used to increase agricultural production and/or lower costs and labor associated with modern productivity.

DETAILED DESCRIPTION OF THE INVENTION

The unique liquid fertilizer composition and process of its production is a novel property of calcium chloride in distinction to other water soluble calcium salts. This was completely unexpected in view of numerous references which instructed a person of ordinary skills in the art that equivalent results could be achieved according to literature references which allow selection of any one of the following calcium salts: nitrate, citrate, tartrate, sulphur, phosphate, chloride, acetate, bromide, carbonate, etc.

In fact, it was only after more than sixty different metal salts were evaluated as suspending agents that it was discovered that calcium chloride provided a new and useful composition of matter. It was surprising to find that calcium nitrate, calcium citrate, calcium acetate, calcium formate and calcium sulfate simply did not give similar results. Typically one to two minutes are required to mix aqueous calcium chloride with ammonium polyphosphate in comparison to the many hours required to swell and mix clay in preparing prior art suspensions. Starting with readily available materials it is possible to mix a six ton liquid fertilizer batch in two minutes.

While it is not known with certainty, it is believed that a complex is formed when calcium chloride and ammonium polyphosphate are mixed in practicing the present invention. This complex would correspond to the original formula $Ca(NH_4)_2 P_2O_7$ having some degree of hydration. However, the calcium chloride also acts as a suspending agent when nitrogen and phosphate sources other than ammonium polyphosphate are used such as orthophosphoric acid, ammonium nitrate and ammonium hydroxide. U.S. Pat. No. 3,526,495 makes disclosure of reacting calcium slag at a temperature between 140° F. and 180° F. The unexpected nature of the present invention is clearly indicated in this reference where it is stated that calcium chloride is suitable for forming a thixotropic gel precipitate in a manner similar to calcium oxide or calcium nitrate. Unexpectedly it has been discovered that calcium chloride does not react in this manner, and instead produces a new and useful product via a new process.

In addition to the discovery that calcium chloride was an inexpensive and readily available suspending agent, it was an even greater discovery to find that the present invention opened up an entirely new field of no-till agriculture. Elimination of clay as a fertilizer suspending agent by the substitution of calcium chloride now allows a combination seed drill and spray application to kill, plant and fertilize in one pass over the field. The need to first kill the vegetation in a first pass and then later to drill in seeds and fertilize in a second pass is eliminated. It was believed that topical herbicides such as the ICI Gramoxone ® herbicide and the Chevron Paraquat ® herbicide are absorbed by the clay suspending agent in conventional fluid fertilizers.

In detail the process of the invention involves the addition of a very soluble calcium salt (calcium chloride) to form a solution instead of a precipitate and thereafter using such a solution as a suspending agent for potash and additional fertilizer and herbicide ingredients. One of the points of novelty of this process is that an initial cloudiness is observed when a concentrated calcium chloride solution is added to the "10-34-0" ammonium polyphosphate which disappears within a minute or so as the ingredients are stirred. This observation is similar to the addition of ammonia to silver nitrate solution wherein initial cloudiness is observed until an excess of ammonia is present to form the complex and produce a clear solution. In any event it is possible to speculate that prior art investigators may have stopped their efforts at the first sign of precipitation and concluded that calcium chloride was equivalent to all other calcium salts.

After the formation of the suspending solution which is step (1) of this process, step (2) involves adding potash (potassium chloride) and water as required. Thus, step (2) requires that the potash be added as a solid to obtain beneficial suspension action. While it is not known with certainty, it is believed that some type of encapsulation of potash particles may occur in step (2).

When steps (1) and (2) of the process are complete, a new and useful fluid fertilizer composition results which is storage stable and can incorporate higher levels of potash along with other fertilizer and herbicide ingredients. The advantages of this clay free composition have been previously described.

Following steps (1) and (2) it is by the addition of a herbicide in step (3) that a composition for no-till agriculture is prepared. In fact, in step (3) it has been discovered that lower amounts of herbicide are required than would be expected. It is believed that the calcium chloride has a synergistic effect with the herbicide.

The following Preparations and Examples illustrate the practice of the invention which has industrial applicability in the field of agriculture and horticulture. All amounts are given in parts by weight unless otherwise indicated.

PREPARATION A

A stock solution was prepared of 50% by weight $CaCl_2.2H_2O$ in tap water. A 3 part portion of the calcium chloride solution was placed in a tank and stirred while a 28.8 part portion of ammonium polyphosphate (Agway "10-34-0") was added along with 5.2 parts of water. After two minutes of stirring a clear solution was produced. No indication of settling or precipitation was observed from a sample removed from the tank.

With continued stirring, 47.4 parts of potash and 15.6 parts water were added. Stirring continued for one minute to prepare a liquid fertilizer suspension.

A fluid pourable suspension of the potassium chloride particles (potash) was observed.

It was thus shown that use of calcium chloride, corresponding to a dosage of 30 pounds $CaCl_2.2H_2O$ per ton of finished suspension, was an effective stabilizer for a fluid suspension of potassium chloride in ammonium polyphosphate fertilizer solution.

Samples of the above suspension containing calcium chloride were poured into glass sample jars and subjected to agitation employing a Burrell Wrist Action Shaker at a setting of "1" for 4 hours. No settling of the suspending KCl particles was observed in these samples.

Several samples of the above fluid fertilizer suspension containing calcium chloride were stored for prolonged periods to observe the stability of this suspension over time. It was found that these fluid fertilizer suspension samples remained fluid and pourable yet showed no perceptible potassium chloride settling after 10 days of static storage.

COMPARISON PREPARATION B

Prior Art Clay Suspension

A liquid fertilizer was prepared containing active ingredients as in Preparation A except that clay was used as the suspending agent instead of calcium chloride. Attapulgite clay (Min-U-Gel 200 from Floridin Company) can be preslurried and allowed to swell for several hours before being used. A total time of 12 hours would be required to disperse the ingredients to prepare a formulation of nutrient value equivalent to formulation A which was prepared in less than 1 hour. The comparison formulation began to settle in 2-3 hours but did not form a firm settling and could be remixed by transfer to the preparation tank. The comparison Preparation B contained 28.8 parts ammonium polyphosphate, 22.3 parts water, 47.4 parts potash and 1.5 parts attapulgite clay.

A fluid suspension of the potassium chloride particles was observed. This experiment corresponded to current industry practice for preparing attapulgite-stabilized suspensions of potassium chloride in ammonium polyphosphate fertilizer. The active dosage of attapulgite in this case was 30 pounds per ton of finished fluid fertilizer suspension.

Samples of the above prepared fluid fertilizer suspension were placed in glass jars and agitated with a Burrell Wrist Action Shaker on a setting of "1" for 4 hours. After this period it was observed that the attapulgite-stabilized fertilizer suspension samples showed significant settling of the potassium chloride particles.

This example thus showed that attapulgite was a less effective stabilizing agent for preparing fluid fertilizer suspensions stable to vibration compared to calcium chloride stabilized of Preparation A.

Upon static storage the attapulgite suspension from above was observed to show significant settling of potassium chloride particles after only 16 hours which was much less effective than the Preparation A.

PREPARATION C

Liquid Fertilizer and Herbicide

Calcium Chloride Suspension

Herbicide is added to Preparation A in an amount effective for topical application.

COMPARISON PREPARATION D

Liquid Fertilizer and Herbicide Clay Suspension

Herbicide is added to Preparation B in an amount effective for topical application.

EXAMPLE 1

Preparation C is applied to a field by a tractor drawn seed drill/fertilizer applicator. The ground cover is killed without adverse effect on the seeds deposited by the seed drill. A crop can be produced without soil erosion with a yield at least equivalent to conventional farming methods.

COMPARISON 1

Comparison preparation D could not be used for a one pass treatment of a field as in Example 1 because the viscosity was too high to allow for spray application when the suspension contained Paraquat ® herbicide. A first application of herbicide and a second application with a seed drill and clay fertilizer suspension were required to obtain results similar to Example 1.

EXAMPLE 2

Both Preparation A and Comparison Preparation B were applied to fields by a tractor drawn fertilizer sprayer. Except for the case of preparation and storage stability of Preparation A, the results obtained were equivalent.

EXAMPLE 3

Other storage stable fluid fertilizer compositions were prepared and tested as in Example 2 and Preparation A except that other nutrients such as ammonium sulfate and sulphur compounds were added. Equivalent results were obtained in storage tests and field application.

This example illustrates the wide utility of the invention to not only prepare "3-10-30" blends but "4-10-22-2.5" blends as well.

EXAMPLE 4

A prior art clay suspension of 3-10-30 was prepared and labeled 52-4. A 3-10-30 suspension with calcium chloride was prepared as in Preparation A and labeled 52-7. Varying amount of the herbicide Paraquat-Gramoxone ® Extra from ICI were added as shown in the table below.

A test crop of oats was planted (broadcast) in soiless mix in 37×53×9.5 cm flats. Eleven days later both control and experimental portions of fluid fertilizer plus Paraquat ® were applied using a 6 liter watering can with coarse nozzle. The height of oat plants at the time of treatment was 10 to 15 cm (4 to 6 inches). It was necessary to use a watering can because the prior art clay suspension could not be applied with a pressurized sprayer. The conditions which existed while applying the treatment were partly sunny with wind less than 5 mph. Table 1 contains results where a toxicity rating of 1-no injury to oats and 10-oats dead.

| Treatment | Herbicide Rate lbs. a. i/A | 1 Day | 2 Days | 3 Days | 6 Days |
|---|---|---|---|---|---|
| None | — | 1.0 | 1.0 | 1.0 | 1.0 |
| Paraquat ® only | 0.38 | 3.7 | 6.0 | 8.3 | 10.0 |
| 52-4 | 0.38 | 6.0 | 7.3 | 9.7 | 10.0 |
| 52-4 | 0.76 | 7.0 | 8.0 | 10.0 | 10.0 |
| 52-7 | 0.38 | 7.3 | 8.7 | 9.0 | 10.0 |
| 52-7 | 0.76 | 8.3 | 9.7 | 10.0 | 10.0 |

Although these results unexpectedly show that the toxicity rate is increased when the Paraquat ® is applied as a fluid fertilizer suspension, this method was discovered to only be applicable to the calcium chloride suspensions of the invention because of the thick and viscous mixture which resulted when the clay suspension was mixed with the Paraquat ®. Fluid suspension 52-7 was easy to pour and handle with or without the Paraquat ®. While it is not readily apparent from the data in Table 1, it was possible to observe necrotic tissue (dead plants) in less than 24 hours only with formulation 52-7 containing the higher level of Paraquat ®.

Overall 52-7 was more effective and easier to handle than the prior art 52-4 fluidized fertilizer suspension in conditions for optimum use in applications in actual fields where no-till agriculture would be practiced.

EXAMPLE 5

The fluid fertilizer formulations used in Example 4 were tested without the addition of herbicide on test crops of oats. Table 2 gives comparative results for applications of fertilizer which would not normally be done in no-till farming since the fertilizer is intended to nourish seeds drilled into the soil and the herbicide is intended to kill ground cover and weeds.

TABLE 2

| Treatment | 1 Day | 2 Days | 3 Days | 6 Days |
|---|---|---|---|---|
| None | 1.0 | 1.0 | 1.0 | 1.0 |
| 52-4 | 1.7 | 3.3 | 5.0 | 8.3 |
| 52-7 | 2.3 | 3.7 | 5.7 | 9.0 |

It is believed that 52-7 (the calcium chloride suspension of the invention) is somewhat more toxic than 52-4 (the clay suspension of the prior art) due to a higher salt level.

These results suggest that ground cover could be killed using even lower levels of herbicide or even none at all if a higher salt level were used.

EXAMPLE 6

A fertilizer suspension was prepared similar to Preparation A except that ammonium polyphosphate was replaced by a nitrogen and phosphate containing solution of orthophosphoric acid, ammonium nitrate and ammonium hydroxide. Then potash was added and suspended by the calcium chloride as in Preparation A. A six ton batch of liquid fertilizer was produced in a total time of two minutes compared to 4 hours for a similar size clay suspension batch. The batch was then transported to agricultural fields and used to increase crop yield in an identical manner to clay suspensions.

EXAMPLE 7

Example 6 was repeated except that ammonium polyphosphate was only partially replaced (50%) by a solution of orthophosphoric acid, ammonium nitrate and ammonium hydroxide. A batch of 3-10-30 liquid fertilizer suspended by calcium chloride gave similar results to Example 6.

What is claimed is:

1. A liquid fertilizer composition comprising ammonium polyphosphate treated with a calcium salt and potassium chloride and other ingredients, characterized in that the ammonium polyphosphate is mixed with from 0.125 to 4.5% by weight calcium chloride to produce an admixture suspending agent for potassium chloride particles wherein the liquid fertilizer composition remains stable in the absence of clay and the calcium chloride functions as a herbicide for ground cover during no-till farming.

2. The composition of claim 1 further comprising more than 10% by weight potassium chloride.

3. The composition of claim 2 where the fertilizer ratio is 3-10-30.

4. The composition of claim 1 further comprising ammonium sulphate.

5. The composition of claim 4 wherein the fertilizer-sulphur composition is 4-10-22-2.5

6. The composition of claim 1 further comprising 1:1-dimethyl-4,4'-bipyridinium dichloride.

7. A process for preparing a storage stable liquid fertilizer comprises the steps:
   (1) preparing separate solutions of ammonium polyphosphate and calcium chloride;
   (2) adding 0.125 to 4.5% by weight dissolved calcium chloride based on the total weight of solids to a stirred solution of ammonium polyphosphate to prepare an admixture suspending agent;
   (3) adding particulate potassium chloride to the admixture to prepare a storage stable liquid fertilizer 8. The process of claim 7 where 1:1-dimethyl-4,4'-bipyridinium dichloride is added after step (3).

9. The process of claim 7 where ammonium sulphate is added after step (3).

10. The process of claim 7 where at least 30 pounds of $CaCl_2.2H_2O$ per ton of finished liquid fertilizer is added in step (2).

11. The process of claim 10 where the finished liquid fertilizer is 3-10-30.

12. The process of claim 9 where the finished liquid fertilizer is 4-10-22-2.5.

* * * * *